United States Patent

Kiener et al.

Patent Number: 5,591,853
Date of Patent: Jan. 7, 1997

[54] PRODUCTS OF A MICROBIOLOGICAL PROCESS FOR THE PRODUCTION OF 2-HALO-PYRIMIDINE-4-CARBOXYLIC ACIDS

[75] Inventors: Andreas Kiener, Visp; Rainer Glöckler, Visperterminen; Gerhard Stucky, Brig-Glis, all of Switzerland

[73] Assignee: Lonza Ltd., Gampel/Valais, Switzerland

[21] Appl. No.: 344,122

[22] Filed: Nov. 23, 1994

Related U.S. Application Data

[62] Division of Ser. No. 158,771, Dec. 1, 1993, abandoned, which is a continuation of Ser. No. 6,489, Jan. 21, 1993, abandoned.

[30] Foreign Application Priority Data

Jan. 24, 1992 [CH] Switzerland ................ 200/92

[51] Int. Cl.$^6$ .................. C07D 239/30; C07D 239/26; C07D 239/34
[52] U.S. Cl. ........................... 544/334; 544/318
[58] Field of Search .................... 544/334, 315, 544/316, 318

[56] References Cited

U.S. PATENT DOCUMENTS

| | | | |
|---|---|---|---|
| 5,104,798 | 4/1992 | Kiener | 435/117 |
| 5,164,397 | 11/1992 | George et al. | 514/275 |
| 5,213,973 | 5/1993 | Hoeks | 425/117 |

FOREIGN PATENT DOCUMENTS

| | | |
|---|---|---|
| 0435749 | 7/1991 | European Pat. Off. . |
| 0442430 | 8/1991 | European Pat. Off. . |
| 0466042 | 1/1992 | European Pat. Off. . |

OTHER PUBLICATIONS

Mamaev et al., Chemical Abstracts, vol. 70, entry 76976 (1968).
Shein et al., Chemical Abstracts, vol. 79, entry 17707 (1972).
George et al., Chemical Abstracts, vol. 115, entry 208015 (1990).
George et al., Chemical Abstracts, vol. 117, entry 48597 (1992).
Chemical Abstracts, vol. 94, No. 1, (Jan. 5, 1981) 3979c.
Kulla et al., Arch. Microbiol., 135, (1983), pp. 1 to 7.
Claus & Walker, J. Gen. Microbiol., 36, (1964), pp. 107–122.

*Primary Examiner*—John M. Ford
*Attorney, Agent, or Firm*—Fisher, Christen & Sabol

[57] ABSTRACT

A 2-halo-pyrimidine-4-carboxylic acid of formula:

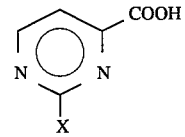

wherein X is a halogen atom, for example, 2-chloro-pyrimidine-4-carboxylic acid. A 2-substituted-pyrimidine-4-carboxylic acid derivative of formula:

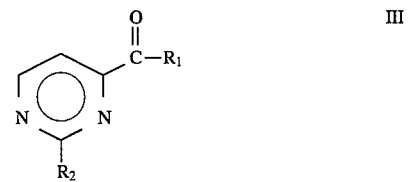

wherein $R_1$ is a halogen atom, $NH_2$—, HO— or a $C_1$–$C_4$ alkoxy group and $R_2$ is a $C_1$–$C_4$ alkoxy group or a halogen atom with the proviso that, if $R_1$ is a HO— group, $R_2$ is not a halogen atom and with the proviso that, if $R_2$ is a halo group, $R_1$ is not an amino group. A 2-substituted-pyrimidine-4-carboxylic acid derivative of formula III wherein $R_1$ is a HO— group and $R_2$ is an ethoxy group.

4 Claims, No Drawings

PRODUCTS OF A MICROBIOLOGICAL PROCESS FOR THE PRODUCTION OF 2-HALO-PYRIMIDINE-4-CARBOXYLIC ACIDS

This is a divisional application of Ser. No. 08/158,771, filed Dec. 1, 1993, now abandoned, which is a continuation application of Ser. No. 006,489, filed on Jan. 21, 1993, now abandoned.

BACKGROUND OF THE INVENTION

1. Field of the Invention

The invention relates to new 2-halo-pyrimidine-4-carboxylic acids of the formula:

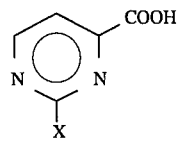

wherein X is a halogen atom, to a process for the production of the new 2-halo-pyrimidine-4-carboxylic acids of the formula I, starting from a 2-halo-4-methylpyrimidine, and to the use of the new 2-halo-pyrimidine-4-carboxylic acids of the formula I for the production of new 2-substituted pyrimidine-4-carboxylic acid derivatives of the formula:

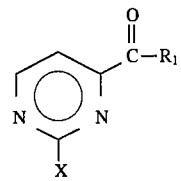

wherein $R_1$ is a halogen atom, $NH_2-$, $HO-$ or a $C_1-C_4$ alkoxy group, and $R_2$ is a $C_1-C_4$ alkoxy group or a halogen atom with the exception that if $R_1$ is $HO-$, $R_2$ is not a halogen atom.

The 2-halo-pyrimidine-4-carboxylic acids of the formula I according to the invention are, in the form of acid amides, important intermediate products for pharmaceutical active ingredients (see European Published Patent Application No. 435,749).

2. Background Art

From the prior art it is known that methyl groups on 5- or 6-ring heterocycles are reacted with microorganisms of genus Pseudomonas to the corresponding carboxylic acid (see European Published Patent Application No. 442,430). However, neither a chemical nor a microbiological process for the production of concrete 2-halo-pyrimidine-4-carboxylic acids is known.

BROAD DESCRIPTION OF THE INVENTION

The main object of the invention is to provide an economical and ecological microbiological process for the production of new 2-halo-pyrimidine-4-carboxylic acids. Other objects and advantages of the invention are set out herein or obvious herefrom to one skilled in the art.

The objects and advantages of the invention are achieved by the compounds and processes of the invention.

The invention involves 2-halo-pyrimidine-4-carboxylic acids of the formula:

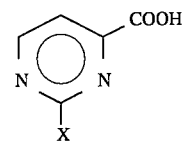

wherein X is a halogen atom. Preferably the 2-halo-pyrimidine-4-carboxylic acid is 2-chloro-pyrimidine-4-carboxylic acid.

The invention also involves a process for the production of 2-halo-pyrimidine-4-carboxylic acids of the formula:

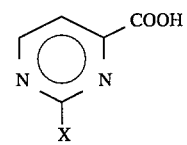

wherein X is a halogen atom. In the process, as a substrate, a 2-halo-4-methylpyrimidine of the formula:

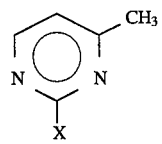

wherein X is a halogen atom, is converted with the xylene-using microorganisms Pseudomonas putida (DSM 6737) or a descendent thereof or a mutant thereof, into the end product according to the formula I. Preferably 2-chloro-4-methylpyrimidine is used as the 2-halo-4-methylpyrimidine of the formula II, wherein X is chlorine. Preferably the enzymes of microorganisms Pseudomonas putida (DSM 6737) are induced with xylene. Preferably the reaction is performed with a single or continuous substrate addition so that the substrate concentration in the culture medium does not exceed 20 percent (w/v). Preferably the reaction is performed at a pH of 4 to 11 and at a temperature of 15° to 50° C.

The invention further involves a process of using 2-halo-pyrimidine-4-carboxylic acids of the formula:

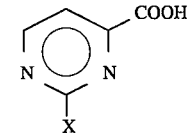

wherein X is a halogen atom, for the production, in a chemical way, of 2-substituted-pyrimidine-4-carboxylic acid derivatives of the formula:

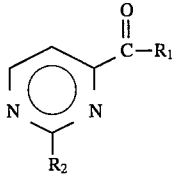

wherein $R_1$ is a halogen atom, $NH_2-$, $HO-$ or a $C_1-C_4$ alkoxy group and $R_2$ is a $C_1-C_4$ alkoxy group or a halogen atom with the exception that if $R_1$ is a $HO-$ group, $R_2$ is not a halogen atom.

The invention also involves 2-substituted-pyrimidine-4-carboxylic acid derivatives of the formula:

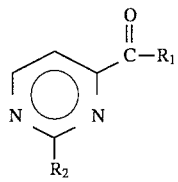

wherein $R_1$ is a halogen atom, $NH_2$—, HO— or a $C_1$–$C_4$ alkoxy group and $R_2$ is a $C_1$–$C_4$ alkoxy group or a halogen atom with the exception that if $R_1$ is a HO— group, $R_2$ is not a halogen atom and with the exception that $R_1$ is not an $NH_2$— group. Preferably, in the 2-substituted-pyrimidine-4-carboxylic acid derivative, $R_1$ is chlorine, a methoxy group or a butoxy group and $R_2$ is chlorine. Also preferably, in the 2-substituted-pyrimidine-4-carboxylic acid derivative, $R_1$ is a HO— group and $R_2$ is an ethoxy group.

The 2-halo-pyrimidine-4-carboxylic acids of the formula I according to the invention are, in the form of acid amides, important intermediate products for pharmaceutical active ingredients (see European Published Patent Application No. 435,749).

DETAILED DESCRIPTION OF THE INVENTION

According to the invention, the process is performed so that as substrate a 2-halo-4-pyrimidine of the formula:

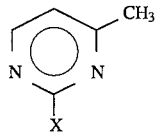

wherein X is a halogen atom, is converted into the end product according to formula I with the xylene-using microorganism *Pseudomonas putida* (DSM 6737) or its descendents or its mutants.

The microorganisms *Pseudomonas putida* (DSM 6737) was deposited on Nov. 10, 1991, with the Deutsche Sammlung von Mikroorganismen und Zellkulturen GmbH. [German Collection for Microorganisms and Cell Cultures GmbH] (DSM), Mascheroderweg 1b, 3300 Braunschweig, Germany.

As substrates for the reaction, commercially available 2-halo-4-methylpyrimidines of the formula:

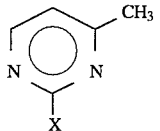

wherein X is a halogen atom, such as, fluorine, chlorine, bromine or iodine, are used. Preferably 2-chloro-4-methylpyrimidine, in which X is chlorine, is used as 2-halo-4-methylpyrimidine.

Suitably the enzymes of the microorganism are induced before the actual biotransformation with xylene or its isomers, such as, p-xylene or m-xylene or their mixtures, preferably with m-xylene. The xylenes used for induction can be present either during the reaction of the substrate or their input can be cut off before the reaction of the substrate. The inductor concentration is usually selected so that it is lower than the minimal inhibiting concentration of the enzyme responsible for the reaction. Depending on the embodiment of the process the input of the compounds used for the induction preferably is cut off during the reaction of the substrate either by stopping the input or by centrifuging off the cells.

The mentioned strain usually grows with xylenes, such as, p-xylene, m-xylene or their mixtures, preferably with m-xylene, as the sole carbon and energy source in a mineral medium as in *Kulla et al.*, Arch. Microbiol., 135, (1983), pages 1 to 7, in a complex medium such as "Nutrient Broth No 2", Oxoid Ltd., G. B., or in a mineral medium, whose composition is indicated in Table 1. The growth substrate according to the data from *Claus and Walker* [J. Gen. Microbiol. 26, (1964), pages 107 to 122] is fed to the medium in the form of gas, and the rate of gassing is suitably 0.5 V/min.

Before the substrate addition, the cells are cultivated in the culture medium up to an optical density of 1 to 200 at 650 nm, preferably up to an optical density of 5 to 100 at 650 nm.

The reaction can take place either by single or continuous substrate addition so that the substrate concentration in the culture medium does not exceed 20 percent (w/v). Preferably the subtrate addition takes place so that the substrate concentration in the culture medium does not exceed 5 percent (w/v).

Depending on the embodiment of the process, the substrate addition can also take place simultaneously with the enzyme inductor, for example, by using a mixture of enzyme inductor and substrate.

The reaction is suitably performed in a pH range of 4 to 11, preferably of 6 to 10.

Suitably the reaction is performed at a temperature of 15° to 50° C., preferably at a temperature of 25° to 40° C. The reaction is usually performed during 1 to 24 hours.

The 2-halo-pyrimidine-4-carboxylic acids, formed in the reaction, of the formula:

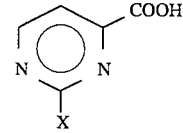

wherein X is a halogen atom, are difficult to obtain chemically and have not been described in the literature. A preferred compound is 2-chloro-pyrimidine-4-carboxylic acid.

The invention also relates to the use of 2-halo-pyrimidine-4-carboxylic acids of formula I, for the production of 2-substituted pyrimidine-4-carboxylic acid derivatives of the formula:

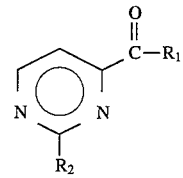

wherein $R_1$ is a halogen atom, $NH_2$—, HO— or a $C_1$–$C_4$ alkoxy group and $R_2$ is a $C_1$–$C_4$ alkoxy group or a halogen atom with the exception that if $R_1$ is a HO— group, $R_2$ is not a halogen atom. The 2-substituted pyrimidine-4-carboxylic acid derivatives of the formula III with the exception that $R_1$ is not an $NH_2$ group, were also not chemically available so far and thus are a component of the invention.

The process for the production of the 2-substituted pyrimidine-4-carboxylic acid derivatives of the formula III takes place chemically, starting from 2-halo-pyrimidine-4-carboxylic acids of the formula I by standard esterification, amidation, halogenation or alcoholysis.

The suitable radicals $R_1$ and $R_2$ of the new 2-substituted pyrimidine-4-carboxylic acid derivatives are:

$R_1$ is halogen, such as, fluorine, chlorine, bromine or iodine, preferably chlorine, or $C_1$–$C_4$ alkoxy, such as, methoxy-, ethoxy-, propoxy- or butoxy-, preferably methoxy- or butoxy-, and $R_2$ is halogen, such as, fluorine, chlorine, bromine or iodine, preferably chlorine, or, if $R_1$ is a HO— group, $R_2$ is $C_1$–$C_4$ alkoxy-, such as, methoxy-, ethoxy-, propoxy- or butoxy-, preferably ethoxy.

EXAMPLE 1

Production of 2-chloro-pyrimidine-4-carboxylic Acid

*Pseudomonas putida* (DSM 6737) was cultured according to European Published Patent Application No. 442,430 with m-xylene, as the sole carbon and energy source, in a 7 liter fermenter with 4.5 l working volume in the mineral medium of Table 1 (see below). The dosage of the growth substrate was coupled with a control by a xylene measurement in the bioreactor exhaust air (see European Published Patent Application No. 442,430). After an optical density of 20 at 650 nm was reached, the inputting of the growth substrate was cut-off and the cell suspension was mixed with 5.0 g (0.04 mol) of 2-chloro-4-methyl-pyrimidine. After 4.5 hours no more initial material was able to be detected by thin-layer chromatography. 2-chloro-pyrimidine-4-carboxylic acid was not further metabolized. The cell-free fermentation solution was concentrated by evaporation up to 100 ml, the pH was adjusted with $H_2SO_4$ to 2.0 and the solution was extracted five times with 100 ml of ethyl acetate each. The organic phase was evaporated to dryness and the residue recrystallized twice from water. 2.2 g (0.014 mol) of 2-chloro-pyrimidine-4-carboxylic acid, corresponding to a yield of 28 percent relative to the 2-chloro-4-methylpyrimidine used, was able to be obtained. Other data for the product was:

$^1$H-NMR: (DMSO-$d^6$, 300 MHz) δ in ppm 2.5, s; 8.05, d; 9.05, d.

TABLE 1

| Medium Composition | |
|---|---|
| $MgCl_2.6H_2O$ | 0.8 g/l |
| $CaCl_2$ | 0.16 g/l |
| $(NH_4)SO_4$ | 2 g/l |
| $NH_4Cl$ | 5 g/l |
| $Na_2SO_4$ | 0.25 g/l |
| $KH_2SO_4$ | 0.4 g/l |
| $Na_2HPO_4$ | 0.9 g/l |
| trace elements | 1 ml/l |
| FeEDTA | 15 ml/l |
| Composition of the trace element solution: | |
| KOH | 15 g/l |
| $EDTANa_2.2H_2O$ | 10 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.2 g/l |
| Composition of FeEDTA: | |
| EDTA $Na_2.2H_2O$ | 5 g/l |
| $FeSO_4.7H_2O$ | 2 g/l |

EXAMPLE 2

Production of 2-chloropyrimidine-4-carboxylic Acid Chloride 12 drops of dimethylformamide was added to a solution of 3.0 g (18.9 mmol) of 2-chloropyrimidine-4-carboxylic acid in 60 ml of thionyl chloride. The reaction was then refluxed for 6 hours. After cooling to room temperature, excess thionyl chloride was removed on a rotary evaporator and the residue distilled (boiling point approximately 100° C./1 mbar). 2.95 g of product, corresponding to a yield of 88 percent relative to the 2-chloropyrimidine-4-carboxylic acid used, which crystallized in the receiving flask, was obtained. The melting point of the product was 52.2° to 53.1° C. Other data for the product was:

$^1$H-NMR: ($CDCl_3$, 300 MHz) δ in ppm 7.25, s; 7.95, d; 9.0, d.

EXAMPLE 3

Production of 2-chloropyrimidine-4-carboxylic Acid Methyl Ester

A solution of 0.5 g (2.82 mmol) of 2-chloropyrimidine-4-carboxylic acid chloride in 10 ml of methanol was stirred for 45 minutes at room temperature. Then the reaction solution was poured on 80 ml of saturated $NaHCO_3$ solution and extracted three times with 50 ml of ethyl acetate each. The combined organic phase was washed with 60 ml of saturated NaCl solution, dried on $Na_2SO_4$ and concentrated by evaporation on a rotary evaporator. After drying on a high vacuum, 0.50 g of product was obtained as white solid, corresponding to a yield of 100 percent relative to the 2-chloropyrimidine-4-caboxylic acid chloride used. The melting point of the product was 93.6° to 96.6° C. Other data for the product was:

$^1$H-NMR: (DMSO, 300 MHz) δ in ppm 2.5, s; 3.95, s; 8.1, d; 9.1, d.

EXAMPLE 4

Production of 2-chloropyrimidine-4-carboxylic Acid Butyl Ester

A solution of 0.52 g (2.93 mmol) of 2-chloropyrimidine-4-carboxylic acid chloride in 10 ml of butanol was stirred for 1.5 hours at room temperature. Then the reaction solution was poured on 80 ml of $NaHCO_3$ solution and extracted three times with 60 ml of ethyl acetate each. The combined organic phase was washed with 60 ml of saturated NaCl solution, dried on $Na_2SO_4$ and concentrated by evaporation on a rotary evaporator. After drying of the product on a high vacuum, 0.53 g of product was obtained as a white solid, corresponding to a yield of 85 percent relative to the 2-chloropyrimidine-4-carboxylic acid chloride used. The melting point of the product was 67.9° to 68.8° C. Other data for the product was:

$^1$H-NMR: ($CDCl_3$, 300 MHz) δ in ppm 1.0, t; 1.5, m; 1.8, m; 4.5, t; 7.25, s; 7.55, d; 8.9, d.

EXAMPLE 5

Production of 2-chloropyrimidine-4-carboxyamide

Ammonia gas was introduced in 20 ml of tetrahydrofuran at −6° C. for 35 minutes. Then it was heated to 10° C. and 1.5 g (8.47 mmol) of 2-chloropyrimidine-4-carboxylic acid chloride was added. The reaction solution was stirred for 45 minutes at room temperature. Then it was concentrated by evaporation on a rotary evaporator, the residue was poured on 90 ml of saturated $NaHCO_3$ solution, and the aqueous phase was extracted three times with 50 ml of ethyl acetate each. The combined organic phase was washed with saturated NaCl solution, dried on $Na_2SO_4$ and concentrated by evaporation on a ratory evaporator. After drying on a high vacuum, 1.07 g of product was obtained as a white solid, corresponding to a yield of 80 percent relative to the 2-chloropyrimidine-4-carboxylic acid chloride used. The melting point of the product was 147.2° to 151.4° C. Other data of the product was:

$^1$H-NMR: (CDCl$_3$, 300 MHz) δ in ppm 6.2, br.s; 7.25, s; 7.7, br.s; 8.1, d; 8.9, d.

EXAMPLE 6

Production of 2-ethoxypyrimidine-4-carboxylic Acid

A suspension of 1.6 g (10 mmol) of 2-chloropyrimidine-4-carboxylic acid in 40 ml of 0.75 molar sodium ethanolate solution in ethanol was refluxed for 4.5 hours. It was allowed to cool to 40° C. and 80 ml of a 1 normal HCl solution was added to the reaction solution. The aqueous phase was extracted three times with 60 ml of ethyl acetate each, the combined organic phase dried with Na$_2$SO$_4$ and concentrated by evaporation on a rotary evaporator. After drying on a high vacuum, 1.55 g of product was obtained as light brown powder, corresponding to a yield of 91 percent relative to the 2-chloropyrimidine-4-carboxylic acid used. The melting point of the product was 177.4° to 178.1° C. Other data of the product was:

$^1$H-NMR: (CDCl$_3$, 300 MHz) δ in ppm 1.5, t; 4.5, m; 7.25, s; 7.75, d; 8.85, d.

What is claimed is:

1. A 2-halo-pyrimidine-4-carboxylic acid of formula:

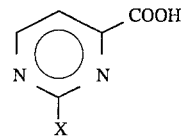

I wherein X is a halogen atom.

2. 2-Chloro-pyrimidine-4-carboxylic acid.

3. A 2-substituted-pyrimidine-4-carboxylic acid derivative of the formula:

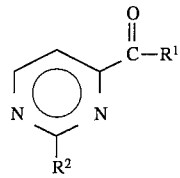

wherein R$_1$ is a halogen atom or a C$_1$–C$_4$ alkoxy group and R$_2$ is a halogen atom or a C$_1$–C$_4$-alkoxy group with proviso that when R$_1$ is a C$_1$–C$_4$-alkoxy group, R$_2$ is not a C$_1$–C$_4$-alkoxy group.

4. The 2-substituted-pyrimidine-4-carboxylic acid derivative according to claim 3 wherein R$_1$ is chloro, a methoxy group or a butoxy group, and R$_2$ is chloro.

* * * * *